United States Patent [19]

deNavarre et al.

[11] 4,302,443

[45] Nov. 24, 1981

[54] NON-IRRITATING ANTIPERSPIRANT

[75] Inventors: Maison G. deNavarre, Orlando; Timothy Meadows, Melbourne, both of Fla.

[73] Assignee: Terry Corporation, Indian Harbour Beach, Fla.

[21] Appl. No.: 123,378

[22] Filed: Feb. 21, 1980

[51] Int. Cl.$^3$ .................. A61K 7/38; A61K 35/78
[52] U.S. Cl. .................. 424/68; 424/DIG. 5; 424/47; 424/69; 424/195
[58] Field of Search .................. 424/195, 68

[56] References Cited

U.S. PATENT DOCUMENTS

| | | | |
|---|---|---|---|
| 3,624,200 | 11/1971 | Moffett | 424/65 |
| 4,049,792 | 9/1977 | Elsnau | 424/66 |
| 4,174,386 | 11/1979 | Spitzer et al. | 424/66 X |
| 4,178,372 | 12/1979 | Coats | 424/195 |

FOREIGN PATENT DOCUMENTS

| | | | |
|---|---|---|---|
| 1251467 | 10/1967 | Fed. Rep. of Germany | 424/68 |
| 1163826 | 5/1958 | France | 424/68 |
| 1156812 | 7/1969 | United Kingdom | 424/68 |

OTHER PUBLICATIONS

Baruzzi et al., Chem. Abs., 1971, vol. 75, pp. 40252p.

*Primary Examiner*—Dale R. Ore
*Attorney, Agent, or Firm*—Duckworth, Allen, Dyer & Pettis

[57] ABSTRACT

An antiperspirant formulation containing an extract from the aloe vera plant that prevents irritation in most persons sensitive to the metallic salts in common use as antiperspirants. A basic formulation consists of a 50% aqueous metallic salt astringent solution of 85 parts by weight and the natural gel of aloe vera of 15 parts by weight. The preferred metallic salt is aluminum chlorohydroxide. The salt may be combined with various other anti-microbial agents, drying agents, fragrances and the like with aloe vera extracts either in the natural gel form or as aloe extract oil to provide formulations for manual or aerosol sprays, roll-ons, creams and the like. The antiperspirant of the invention permit use by most persons formerly unable to tolerate many antiperspirants due to irritation of the skin.

9 Claims, No Drawings

NON-IRRITATING ANTIPERSPIRANT

BACKGROUND OF THE INVENTION

1. Field of the Invention

The present invention relates to antiperspirant formulations having anti-irritant properties, and more particularly to such formulations having aloe vera consititutents.

2. Description of the Prior Art

The majority of the antiperspirants in use at the present time utilize metallic salts as the astringent agent. The most common salt that is non-toxic and permitted by The Food and Drug Administration is aluminum chlorohydroxide. The maximum antiperspirant effect of this aluminum salt in water solutions occurs at a pH in the range of 4.0–4.5. As commonly used, the aluminum chlorohydroxide antiperspirants produce irritations in some users. For example, the 1977–1978 NEISS report published by the Federal Government indicates that from 7% to 10% of the population experiences such irritation. Of this group, it is estimated about four percent are unable to use any antiperspirants because of severe irritation effects. The irritating effects have been thought to result from the acidity of the aluminum salt on the more sensitive skins.

The term "antiperspirant" is often used when describing either an antiperspirant or a deodorant, although in fact the two serve different functions. A deodorant does nothing to reduce the flow of perspiration per se but contains typical antiseptics or bactericides which destroy or prevent activity of the surface bacteria that cause odor. An antiperspirant acts as a deodorant by destroying skin bacteria and also by reducing the flow of perspiration through the astringent action of the metallic salt content. Although the exact operation of metallic salts such as aluminum, zirconium, or zinc in reducing perspiration is not known, one theory suggests that such antiperspirants irritate the sweat ducts causing them to swell, thus blocking off the flow of perspiration. This theory is consistent with the observed side effect of skin irritation arising from the use of antiperspirants.

The drug and cosmetic industry has noted the tendency of many people to switch brands of products and it is believed that skin irritation is the main reason for such switching. Thus, a need exists for antiperspirant formulations which control perspiration but which do not create excessive skin irritation.

SUMMARY OF THE INVENTION

We have discovered that antiperspirant formulations which include aloe vera will provide products which do not irritate the skin and can therefore provide help to the many persons who in the past have been unable to utilize antiperspirants. Although it is not known which of the many constituents of aloe is responsible for the anti-irritant effect when aloe vera is combined with aluminum salts, there are a number of such constituents which have resulted in aloe vera being used as a healing agent for several thousand years. For example, the natural complex of mucopolysaccharides, various known quinones, anthraquinones, sugars such as the pentosans and hexosans, and galacturonates found in aloe vera, many if not all of which are in some way complexed with the polysaccharides, may act as natural healing elements and in some manner counteract the irritating effect of the metallic salts. In addition to the above, at least four enzymes, traces of steroids, volatile terpenes, sapogenins, glucosamines, glycosides, flavones and hecogenins are known to be present and may produce physiological effects on the skin.

We have determined that aloe vera may be utilized in antiperspirant formulations as the natural gel in the form found in the leaves of the plant. Additionally, aloe oil extract obtained from the leaves is useful in other formulations. The most basic formulation, in accordance with our invention, is a product including aluminum chlorohydroxide as the astringent in an aqueous solution with about 15% by weight of the natural gel of aloe vera. Results of tests on a number of subjects who experience irritation from currently available antiperspirant formulations showed that the formulations of the invention could be used without irritation. Additionally, many persons who formerly were unable to use any antiperspirants were able to utilize the formulation of the invention with no untoward reactions.

Therefore, it is a principle object of the invention to provide an effective antiperspirant which does not produce irritation of the skin.

It is another object of the invention to provide an antiperspirant utilizing a metallic salt such as aluminum chlorohydroxide in combination with an extract of the aloe vera plant to produce a non-irritating antiperspirant.

It is still another object of the invention to provide an anti-irritant antiperspirant which may be safely utilized by persons previously unable to use prior art antiperspirants due to irritating effects.

It is yet another object of the invention to provide a non-irritating antiperspirant in which the anti-irritant agent is derived from the aloe vera plant and which does not affect the normal deodorizing or antiperspirant effect of the metallic salt.

It is a further object of the invention to provide a non-irritating antiperspirant in which the natural gel of aloe vera is the anti-irritant agent.

It is yet a further object of the invention to provide a non-irritating antiperspirant in which the oil extract of the aloe vera leaf is the anti-irritant agent.

These and other objects and advantages of the invention may be noted from the following detailed description.

DETAILED DESCRIPTION OF THE PREFERRED EMBODIMENT

We have found that a variety of products for use as an antiperspirant and deodorant can be formulated using extracts from the aloe vera plant which are effective for such purposes and which do not cause skin irritation in persons otherwise sensitive to antiperspirants containing metallic salts. For example, such products in accordance with our invention can be produced in the forms of: manual spray; aerosol spray; roll-on; stick; cream; and powder.

A basic formulation in accordance with our invention is an antiperspirant defined by the following general composition ranges:

|  | Parts by Weight | Preferred Parts by Weight |
| --- | --- | --- |
| Aqueous metallic salt astringent (50%) | 75–95 | 85 |
| Aloe vera gel | 5–25 | 15 |

In addition to the metallic salt astringent and aloe vera extract, other constituents are preferably added to produce an effective non-irritating antiperspirant in any of several forms and to improve its efficiency. A generic formulation with preferred agents may be described as follows:

| | PARTS BY WEIGHT |
|---|---|
| Extract of the aloe vera plant | 4–25 |
| Aqueous metallic salt astringent (50% solution) | 20–40 |
| Vehicle | 30–60 |
| Plasticizer | 1–15 |
| Surfactant | 0–2 |
| Emulsifying agent | 0–15 |
| Suspending agent | 0–2 |
| Fragrance | 0–0.5 |

By varying the proportions and the type of each of the above agents within the indicated ranges, the aniperspirant of the invention may be prepared in liquid form for manual or aerosol spray application, in a form for roll-on application, and in a cream form. As examples, the following represent illustrative preferred embodiments of such forms of the invention. However, the examples are not to be construed as limitations thereon in any manner. Thus, the proportions of ingredients may be varied, different combinations thereof may be used, and other changes may be made without departing from the spirit and scope of our invention.

EXAMPLE 1

A manual-spray type non-irritating antiperspirant was prepared having the following formulation:

| | PARTS BY WEIGHT |
|---|---|
| Aloe vera gel | 15.0 |
| Aqueous aluminum chlorohydroxide (50%) | 24.0 |
| SDA-40A denatured alcohol | 58.0 |
| Propylene glycol | 1.0 |
| [1]Arlamole E | 1.0 |
| Fragrance | 0.1 |
| Water | Q.S |

[1]PEG-15 stearyl ether

In this example, the vehicle is denatured alcohol acting as a solvent and also providing a drying function. Propylene glycol acts as a plasticizer and Arlamole E as a surfactant.

The denatured alcohol, Arlamole E and the fragrance were dissolved together. When the solution cleared, the aloe vera gel, the propylene glycol and water were added and stirred until the mixture became clear.

EXAMPLE 2

A roll-on non-irritating antiperspirant was prepared having the following formulation.

| | PARTS BY WEIGHT |
|---|---|
| Aloe extract oil | 4.0 |
| Glycerin | 2.0 |
| [2]Amerchol L-101 | 1.0 |
| [3]Solulan 98 | 2.0 |
| Cetyl alcohol | 1.0 |
| [4]Arlacel 165 | 4.0 |
| [5]Veegum K | 1.0 |
| Aqueous aluminum chlorohydroxide (50%) | 36.0 |
| Water and preservatives | Q.S. |

[2]Lanolin alcohol and mineral oil (Amerchol, Inc.)
[3]Lanolin derivative (Amerchol, Inc.)
[4]Glycerol stearate and PEG 100 stearate (ICI America)
[5]Magnesium silicate which forms gel with water (R. T. Vanderbilt & Co.)

Here, water is the vehicle with Veegum K acting as a suspending agent. Glycerin is a plasticizer, and Amerchol, Solulan, cetyl alcohol and Arlacel are emulsifiers.

The water was heated to 90° C. and the Veegum K dispersed therein. When the Veegum was fully hydrated, the following were added and mixed: aloe extract oil; Amerchol L-101; Solulan 98; cetyl alcohol; and Arlacel 165 while maintaining the constituents at 80° C. The mixture was cooled to 45° C. and the aluminum chlorohydroxide added.

EXAMPLE 3

A cream-type non-irritating antiperspirant was prepared having the following formulation:

| | PARTS BY WEIGHT |
|---|---|
| Stearic acid | 14.0 |
| Mineral Oil | 1.0 |
| Beeswax | 2.0 |
| [6]Myrj 52 | 5.0 |
| [7]Atlas G-2162 | 5.0 |
| Aqueous Sorbitol (70%) | 6.0 |
| Aloe vera gel | 10.0 |
| Aqueous aluminum chlorohydroxide (50%) | 36.0 |
| Water and preservatives | Q.S. |

[6]PEG 40 stearate (ICI America)
[7]PEG 25 propylene glycol stearate

Stearic acid and water comprise the vehicle in this example. Mineral oil, beeswax and Sorbitol act as plasticizers and Myrj 52 and Atlas G-2162 are emulsifiers.

The stearic acid, mineral oil, beeswax and Myrj 52 were heated to 80° C. and the Atlas G-2162, Sorbitol, aloe vera gel and water were heated to 80° C. The mixture containing the aloe vera gel was added to the mixture containing the beeswax and mixed until the combination cooled to 45° C. At this temperature, the aluminum chlorohydroxide was added.

Although the above Examples, which represent illustrative formulations of our invention, show spray, roll-on and cream types, it will be obvious to those of skill in the art that the non-irritating antiperspirants of the invention can be produced also in stick form, powder form, and as an aerosol spray.

We claim:

1. A non-irritating antiperspirant composition comprising:
    a 50% solution of aluminum chlorohydroxide in an amount from about 75 to about 95% by weight; and
    an extract of the aloe vera plant in an amount from about 5 to 25% by weight.

2. The composition as defined in claim 1 in which said extract is the natural aloe vera gel.

3. A non-irritating antiperspirant composition comprising in combination: p1 a 50% solution of aluminum chlorohydroxide in an amount within the range from about 20 to about 30% in weight;
    an extract of the aloe vera plant in an amount within the range from about 4 to about 25% by weight;

a solution of stearic acid in water in an amount within the range from about 30 to about 60% by weight; and a combination of mineral oil, beeswax and aqueous sorbitol in an amount within the range from about 1 to about 15% by weight.

4. The composition as defined in claim 3 further comprising a combination of polyethylene glycol 40 stearate and polyethylene glycol 25 propylene glycol stearate in an amount within the range from about 5 to about 15%.

5. The composition as defined in claim 4 further comprising magnesium silicate which forms a gel with water in an amount within the range from about 0.5 to 2%.

6. A non-irritating antiperspirant composition as defined in claim 3 further comprising:
   polyethylene glycol 15 stearyl ether in an amount within the range from about 0.5 to about 2%; and
   a fragrance agent in an amount within the range from about 0.05 to about 0.5%.

7. The antiperspirant composition as defined in claim 4 is a cream form in which:
   said 50% solution of aluminum chlorhydroxide is in an amount of about 36% by weight;
   said extract is the natural aloe vera gel in an amount of about 10% by weight; p1 said stearic acid solution is about 30% by weight;
   said combination of mineral oil, beeswax, and aqueous sorbitol is about 14% by weight; and
   said combination of polyethylene glycol 40 stearate and polyethylene glycol 25 propylene glycol stearate is about 10% by weight.

8. The composition as defined in claim 7 in which said stearic acid solution comprises stearic acid in an amount of about 14% by weight and water in an amount of about 16% by weight;
   said mineral oil is about 1% by weight;
   said beeswax is about 2% by weight;
   said aqueous sorbitol is about 6% by weight;
   said polyethylene glycol 40 stearate is about 5% by weight;
   said polyethylene glycol 25 propylene glycol stearate is about 5% by weight.

9. A non-irritating antiperspirant composition in a form suitable for roll-on application comprising in combination:
   a 50% solution of aluminum chlorhydroxide in an amount of about 36% by weight;
   an extract of the aloe vera plant in an amount of about 4% by weight;
   magnesium silicate in an amount of about 1% by weight, said magnesium silicate forming a gel with water;
   a combination of glycerol stearate in an amount of about 4% by weight, cetyl alcohol in an amount of about 1% by weight, lanolin derivative in an amount of about 2% by weight, and lanolin alcohol-mineral oil in about 1% by weight; and
   water in an amount of about 51% by weight.

* * * * *